United States Patent [19]

Adair

[11] 4,362,246
[45] Dec. 7, 1982

[54] METHOD OF TREATING COLLECTED MAMMAL SEMEN AND SEPARATING SPERM INTO X Y COMPONENTS

[76] Inventor: Edwin L. Adair, 191 East Orchard, Littleton, Colo. 80123

[21] Appl. No.: 168,078

[22] Filed: Jul. 14, 1980

[51] Int. Cl.$^3$ .............................................. B07G 5/02
[52] U.S. Cl. .................................... 209/3.3; 209/578; 209/606; 23/230 B
[58] Field of Search ................ 209/3.1, 3.2, 576, 578, 209/606, 3, 11; 23/230 B; 204/299, 180 R

[56] References Cited

U.S. PATENT DOCUMENTS

| | | | |
|---|---|---|---|
| 3,791,517 | 2/1974 | Friedman | 209/3.1 |
| 3,976,197 | 8/1976 | Bhattacharya | 209/3.1 |
| 4,155,831 | 5/1979 | Bhattacharya | 23/230 B |
| 4,225,405 | 9/1980 | Lawson | 23/230 B |

Primary Examiner—Allen N. Knowles

Attorney, Agent, or Firm—Fields, Lewis, Pittenger & Rost

[57] ABSTRACT

A method of treating mammal semen for use in artificial insemination is provided. Human saliva is added to the semen as an anti-coagulant. For mammals other than primates and voles, sperm-free human semen is added to the mammal semen as a cell membrane diffusion material so that a dye such as quinicrine or quinicrine mustard will be absorbed by the Y chromosome. The semen is then fed in a narrow stream through a detection chamber where it is irradiated with ultraviolet light causing the Y chromosomes to fluoresce. The stream is fed from the detection chamber through a fluidic amplifier wherein the stream is switched in response to whether the detected chromosome is fluorescent or non-fluorescent so that the fluorescent Y chromosome is directed through one outlet port and collected and the non-fluorescent X chromosome is directed through a second outlet port and collected.

13 Claims, No Drawings

METHOD OF TREATING COLLECTED MAMMAL SEMEN AND SEPARATING SPERM INTO X Y COMPONENTS

TECHNICAL FIELD

This invention relates to an improved method of preserving collected mammalian semen and separating the sperm into X and Y components so that a female of the species may be artificially inseminated with separated semen to produce offspring of a desired and predetermined sex. This invention is particularly useful for preserving cattle semen and separating it so that semen having only X chromosomes can be used for producing dairy cattle herds and semen having only Y chromosomes can be used for producing beef herds. This invention also has usage in breeding horses and other animals.

BACKGROUND ART

It is well known that in primates, such as humans and gorillas, the Y chromosome of sperm tends to fluoresce to a special brightness when stained with a dye such as quinicrine or quinicrine mustard whereas the X chromosome of sperm will not fluoresce. It is also known that the sperm of most other animals will not normally be subject to this selective staining unless a cell wall diffusion material or agent, such as an appropriate enzyme or chemical, is used to facilitate passage through the cell wall or cell membrane so that the dye can enter the cell. A commercially available chemical for this purpose is dimethylsulfoxide. It is also known that by adding papaya protease to the sperm of horses and bulls, the cell membrane can be penetrated by the dye so that selective identification of the X and Y chromosomes can be accomplished under a microscope. A disclosure of this technique is found in U.S. Pat. No. 4,155,831 entitled "Thermal Convection Counter Streaming Sedimentation and Forced Convection Galvanization Method and Apparatus for Controlling the Sex of Mammalian Offspring", issued May 22, 1979 to Bhairab C. Bhattacharya. Such a process has been used in the prior art to determine the success ratio in separating X and Y sperm by other known methods.

A device for identifying and then separating live blood cells from dead blood cells is disclosed in U.S. Pat. No. 3,791,517 for "Digital Fluid Amplifier Particle Sorter", issued Feb. 12, 1974 to Mitchell Friedman. It is suggested in this patent that the separating of the particles may be done, if desired, by use of selective fluorescent radiation responses from the particles.

However, no known way has been suggested in the prior art for staining Y chromosomes so that they fluoresce and using the fluorescence as a means of separating the X chromosomes into one container and the Y chromosomes into another container. This is of particular significance in cattle breeding wherein it is desired to have a large number of female offspring with dairy cattle and a large number of male offspring with beef cattle. Also, such a separating technique, if available, would have wide application in any situation where predetermination of the sex of the offspring would be desirable.

The other known methods of separation depend on existing physical differences between sperm containing either the X or Y chromosome. The difference includes slightly larger size and heavier weight of the sperm containing the X chromosome, generally higher velocity of movement of the Y chromosome containing sperm, and an apparent dense negative electrical surface charge on the X chromosome. However, the methods of separation of sperm utilizing these physical properties have, for the most part, been only partially successful with separation percentages ranging from 60% to 80%. Thus, there is a very great need for a method of sperm separation which is virtually 100% accurate and which can be done very rapidly. Furthermore, in order to accomplish separation, it is necessary to maintain or get the semen which has been collected in a fluid non-coagulated condition before the separation can be accomplished.

DISCLOSURE OF INVENTION

In accordance with this invention, a method of treating semen for use in artificial insemination is provided wherein the semen is collected from a mammal and treated by adding an anti-coagulant, such as mammal saliva, to prevent coagulation and hasten liquefaction. In particular, human saliva has been found very satisfactory for this purpose and is readily available. The semen is then diluted with a diluting solution and stored in a water bath at substantially the body temperature of the mammal.

When the semen is of mammals other than primates and voles, a cell wall cell membrane diffusion material, such as sperm-free human semen, must be added to the mammal semen so that a fluorescent dye can penetrate the cell membrane of the Y chromosome. The dye will penetrate the cell membrane of primates and vole semen without prior preparation. Conveniently, the dye may be quinicrine or quinicrine mustard.

The semen is then irradiated with ultraviolet light so that the Y chromosome cells will fluoresce as they are moved substantially single file in a stream through a detection chamber. The detection chamber senses the presence of either fluorescent or non-fluorescent cells and provides an output signal in response to the sensed cell which varies according to whether the cell is fluorescent or non-fluorescent. The stream then passed through a fluidic amplifier and the stream is switched in response to each sensed cell in the detection chamber to direct the sensed cell to one of two outlet ports so that the fluorescent cells are directed through one outlet port and collected and the non-fluorescent cells are deflected through the other outlet port and collected. In this way, the X and Y chromosomes can be effectively separated into separate containers for use in artificial insemination of female animals in order to produce the desired sex in the offspring.

It will be apparent that this method of treating mammal semen and separating X and Y chromosomes is rapid and highly efficient.

Additional advantages of the invention will become apparent from the detailed description which follows.

BEST MODE FOR CARRYING OUT THE INVENTION

Semen is first collected from a mammal in any manner which is known to one skilled in the art. For example, with cattle and horses, teaser animals or electrical stimulation may be used. The various methods of collecting semen from animals is explained in conventional veterinarian reference texts.

The collected semen is placed in a clean, sterile container and may be treated with an enzyme solution to hasten liquefaction. Cattle semen for example is highly viscous and will not flow in a stream as necessary for separation unless an anti-coagulant is added and a dilutant is also added. Advantageously, it has been found that one of the best enzyme solutions and one of the most physiologically compatible is mammal saliva, and particularly human saliva. In practice, about 1 ml of human saliva is added to each quantity of about 2.0 ml to about 3.5 ml of semen. If the quantity of human saliva added is significantly less than 1 ml, the reaction will be too slow. However, an amount larger than 1 ml will have no adverse effect, but is unnecessary.

The semen is then diluted with any known commercially available semen diluting solution on about a 1:1 basis. Commercially available semen diluting solutions contain egg yolk, glycerol, glucose and citrate. Preparation of these solutions is set forth in *Fertility and Sterility* by Berman and Sasada, published in 1966. One such anti-coagulant is alpha-amylase. The semen is then stored in a water bath at approximately the body temperature of the animal. This is between about 35° C. and about 38.5° C., but is usually about 37° C. If the temperature is substantially above or below this range, sperm mobility will decrease and the survivial rate of the sperm will decrease below acceptable limits.

When it is time to selectively identify and separate the X and Y chromosomes in semen if it is from mammals other than primates and voles, a cell membrane diffusion material must be added to the collected semen so that a dye can penetrate the cell membrane of the Y chromosome causing it to fluoresce under ultraviolet light. The dye will penetrate the cell membrane of the Y chromosome in primate and vole semen without further treatment. One cell membrane diffusion material which has been found satisfactory is DMSO, commonly known as dimethylsulfoxide and sometimes referred to as disulfomethoxide. It has been found that the addition of about 0.05 ml of DMSO to a quantity of about 2.0 ml to about 3.5 ml of semen provides sufficient penetration of the cell membrane by the dye.

Another cell membrane diffusion material which has been found quite satisfactory is sperm-free human semen. The sperm-free human semen is added in a quantity of about 0.5 ml human semen to a quantity of about 2.0 ml to about 3.5 ml of mammal semen. If either DMSO or human semen is added in quantities substantially below the indicated ranges, the diffusion of the dye will be very slow whereas if the amounts added are substantially above the indicated ranges, the DMSO and human semen will have a toxic effect and kill substantial numbers of the sperm.

The dyes which has been found most satisfactory are taken from the group consisting of quinicrine, quinicrine hydrochloride, quinicrine dihydrochloride and quinicrine mustard. When quinicrine hydrochloride of quinicrine dihydrochloride is used, it is diluted in a solution of ion-free distilled water to a strength in the range of about 0.05% to about 5.0%. The most satisfactory range has been found to be between about 0.5% and about 1.0% in solution. When quinicrine mustard is used, it is diluted with ion-free distilled water to a solution having a strength in the range of about 0.001% to about 0.01% whereas the optimum range is about 0.005% solution. If the solutions are substantially below the indicated range in concentration, the dye will take too long to stain, whereas if the solutions are substantially above the indicated ranges in concentration, the dye will have a toxic effect and kill substantial numbers of the sperm. The dye solution is put in contact for a period of at least several minutes, but usually for a period of at least 15 minutes to assure good dye penetration. Confirmation of staining is obtained by separating a small part of the specimen and checking for staining under a fluorescent microscope.

After the semen has been thus treated, it can be fed through a digital fluidic amplifier particle sorter such as that described in the above-mentioned U.S. Pat. No. 3,791,517 to Friedman. This device is sold under the trademark "CYTOFLUOROGRAF" by Ortho Instruments, Inc. of Westwood, Mass., U.S.A. The disclosure of this patent is hereby incorporated by reference. By using this apparatus, the difference in fluorescence of the chromosomes entrained in a stream of diluted semen is detected and the resultant different signals which are produced as a result of this detection are used to control a fluidic amplifier located downstream to switch the X chromosomes to one outlet port and the Y chromosomes to a second outlet port so they can be separated and collected.

In particular, the semen is fed in a very narrow stream so that the chromosomes in the semen move essentially single file past a laser light beam which is provided with an ultraviolet filter. The laser projects a very narrow beam in which a pattern of illumination of the beam, when it strikes the particle, appears as a thin line of light transverse to the stream of chromosomes. Electrical photoresponsive pick-up elements are arranged around the outside of the detection chamber through which the stream passes to detect any scattering of light due to the ultraviolet light striking a fluorescent Y chromosome. The excitation wavelength of the laser beam is in the range of 457 nm to 488 nm. The emission wavelength from the fluorescent Y chromosome will be around 351 nm. The fluid amplifier includes a transducer which is responsive to any scattering of light due to fluorescence of a Y chromosome which will create a turbulance in the stream to cause a "wall attachment effect" as is well known in fluidics. Thus, any non-fluoresce X chromosome will pass along the stream uninterrupted and out a first outlet port whereas fluoresce Y chromosomes will be diverted due to reaction of the transducer to the scattered light causing them to be diverted and pass through a second outlet port. By this means, the semen can be separated into X and Y components and separately collected for artificial insemination of an animal at a future time wherein the sex of the offspring will be predetermined. The separation accuracy of this method is extremely high compared with the 60% to 80% separation possible with other techniques. In practice, using this technique, the separation effectiveness is nearly 100% and is at least greater than 98%. After separation, the sperm may be frozen for use at a future time in a manner which is will known.

From the foregoing, it can be seen that a highly novel and efficient method has been provided for preparing mammal semen for separating the X and Y chromosomes so that a female animal such as a cow or horse can be artificially inseminated and the sex of the offspring predetermined. Of course, it will be understood that the use of this technique would have application with respect to any mammal.

The invention has been described in detail with particular reference to a preferred embodiment thereof, but it will be understood that variations and modifications can be effected within the spirit and scope of the invention.

What is claimed is:

1. A method of preserving semen for use in artificial insemination comprising the steps of:
   collecting semen from a mammal;
   treating the mammal semen by adding mammal saliva to prevent coagulation;
   diluting the semen with a diluting solution; and
   storing the semen in a water bath at substantially the body temperature of the mammal.

2. The method, as claimed in claim 1, wherein:
   human saliva is added to the mammal semen to prevent coagulation.

3. The method, as claimed in claim 1, wherein:
   a quantity of about 1.0 ml of human saliva is added to a quantity of about 2.0 ml to about 3.5 ml of mammal semen.

4. The method, as claimed in claim 1, wherein:
   the mammal semen is diluted on about a 1:1 ratio.

5. The method, as claimed in claim 1, wherein:
   the treated and diluted mammal semen is stored at a temperature in the range of about 35° C. to about 38.5° C.

6. The method, as claimed in claim 4, wherein:
   the treated and diluted semen is stored at a temperature of about 37° C.

7. A method of separating X and Y chromosomes in mammal semen comprising the steps of:
   collecting semen from the mammal;
   adding about 1.0 ml of mammal saliva to about 2.0 ml to about 3.5 ml of mammal semen to prevent coagulation;
   diluting the semen on a 1:1 ratio with a diluting solution;
   maintaining the temperature of the treated and diluted semen at a temperature of about 37° C.;
   adding a cell membrane diffusion material to the semen so that a dye can penetrate the cell membrane of the sperm containing the Y chromosome;
   adding a dye to the semen to cause only the Y chromosome to fluoresce under ultraviolet light;
   irradiating the semen with ultraviolet light;
   moving the semen in a stream through a detection chamber;
   sensing the presence of either a fluorescent Y chromosome or a non-fluorescent X chromosome in the detection chamber;
   providing an output signal in response to the sensed chromosome which varies according to whether the chromosome is fluorescent or non-fluorescent;
   passing the stream from the detection chamber through a fluidic amplifier; and
   switching the stream in response to each sensed chromosome to one of two outlet ports so that the fluorescent Y chromosomes are directed through one outlet port and collected and the non-fluorescent X chromosomes are directed through the other outlet port and collected.

8. The method, as claimed in claim 7, wherein:
   about 0.05 ml of DMSO is added to about 2.0 ml to about 3.5 ml of semen as the cell membrane diffusion material.

9. The method, as claimed in claim 7, wherein:
   aboout 0.5 ml of sperm-free human semen is added to about 2.0 ml to about 3.5 ml of semen as the cell membrane diffusion material.

10. The method, as claimed in claim 7, wherein:
    the mammal saliva is human saliva which is added to the semen.

11. The method, as claimed in claim 7, wherein:
    the dye is from the group consisting of quinicrine, quinicrine hydrochloride, quinicrine dihydrochloride and quinicrine mustard.

12. A method of separating sperm containing X and Y chromosomes from semen which has been dyed to cause penetration of the dye only into the Y chromosome, comprising the steps of:
    moving the semen in a stream through a detection chamber;
    irradiating the semen with ultraviolet light;
    sensing the presence of either a fluorescent or non-fluorescent chromosome in the stream in the detection chamber;
    providing an output signal in response to the sensed chromosomes which varies according to whether the chromosome is fluorescent or non-fluorescent;
    passing the stream from the detection chamber through a fluidic amplifier; and
    switching the stream in response to each sensed chromosome in the detection chamber to direct the sensed chromosome to one of two outlet ports so that the fluorescent Y chromosomes are directed through one outlet port and collected and the non-fluorescent X chromosomes are directed through the other outlet port and collected.

13. The method, as claimed in claim 12, wherein:
    said semen is irradiated with ultraviolet light having a wavelength between about 457 nm and about 488 nm.

* * * * *